(12) United States Patent
Atkinson et al.

(10) Patent No.: US 7,507,418 B2
(45) Date of Patent: Mar. 24, 2009

(54) ADENOVIRUS STATUS AS A PREDICTOR OF BODY COMPOSITION CHANGE, DISEASE STATUS, AND TREATMENT OUTCOMES

(75) Inventors: Richard L. Atkinson, Mechanicsville, VA (US); Nikhil V. Dhurandhar, Baton Rogue, LA (US)

(73) Assignee: Obetech, LLC, Richmond, VA (US)

( * ) Notice: Subject to any disclaimer, the term of this patent is extended or adjusted under 35 U.S.C. 154(b) by 0 days.

(21) Appl. No.: 11/530,289

(22) Filed: Sep. 8, 2006

(65) Prior Publication Data

US 2007/0077584 A1    Apr. 5, 2007

Related U.S. Application Data

(60) Provisional application No. 60/715,182, filed on Sep. 9, 2005.

(51) Int. Cl.
| | |
|---|---|
| A61K 39/235 | (2006.01) |
| A61K 39/00 | (2006.01) |
| A61K 39/42 | (2006.01) |
| A61K 35/14 | (2006.01) |
| C12Q 1/70 | (2006.01) |
| G01N 33/53 | (2006.01) |
| A61K 39/187 | (2006.01) |

(52) U.S. Cl. .............. 424/233.1; 424/147.1; 424/159.1; 424/184.1; 424/529; 435/5; 435/7.1

(58) Field of Classification Search .................. None
See application file for complete search history.

(56) References Cited

U.S. PATENT DOCUMENTS 6,664,050 B1 * 12/2003 Atkinson et al. ................ 435/6
2007/0218081 A1 * 9/2007 Atkinson .................. 424/233.1

OTHER PUBLICATIONS

Sequence alignment of translated protein from SEQ ID No. 1 of U.S. Appl. No. 11/099,679 and SEQ ID No. 1 of U.S. Appl. No. 11/530,289, conducted on Nov. 3, 2007.*

Gal Trieu, Phentermine for weight loss, 2003, Healthy Weight Forum, (http://www.healthyweightforum.org/eng/articles/phentermine/) accessed on Nov. 3, 2007.*

DeNoon D., Obesity Virus: More, Bigger Fat Cells: Common Virus Boosts Fat-Cell Production—and Makes Fat Cells Fatter, 2007, WebMD Medical News, accessed from (http://www.webmd.com/diet/news/20070820/obesity-virus-more-bigger-fat-cells) on Nov. 1, 2007.*

Guardian Newspaper, Obesity Virus-A Factor in Overweight?, 2003, accessed from (http://www.annecollins.com/weight_health/obesity-virus.htm) on Nov. 1, 2007.*

Kolakowski N., The Obesity Virus?, Researchers suggest viral infection may cause obesity, 2005, DOC News, vol. 2, No. 1, p. 13.*

Venuto T., Infectobesity-Fact and Fiction About The Obesity Virus, 2007, accessed from (http://dietandbody.com/did-you-know/2007/08/obesity-virus-facts.html) on Nov. 1, 2007.*

Dhurandhar et al., Human Adenovirus Ad-36 Promotes Weight Gain in Male Rhesus and Marmoset Monkeys, 2002, Nutritional Immunology, vol. 132, pp. 3155-3160.*

Atkinson et al., Human adenovirus-36 is associated with increased body weight and paradoxical reduction of serum lipids, 2006, International Journal of Obesity, vol. 29, pp. 281-286.*

Dhurandhar et al., Human Adenovirus Ad-36 Promotes Weight Gain in Male Rhesus and Marmoset Monkeys1,2, 2002, The Journal of Nutrition, vol. 132, 3155-3160.*

* cited by examiner

Primary Examiner—Bruce Campell
Assistant Examiner—Benjamin P Blumel
(74) Attorney, Agent, or Firm—Townsend and Townsend and Crew LLP

(57) ABSTRACT

Infection with obesifying adenoviruses in animals and humans may be used to predict changes in body weight and disease status. More particularly, infection with certain adenoviruses, such as adenovirus type 36 (Ad-36) and adenovirus type 37 (Ad-37) may cause removal of the normal equilibrium factors that control fat cell metabolism and may make individuals more responsive than normal individuals to perturbations, which cause body composition change including weight gain or weight loss.

17 Claims, 21 Drawing Sheets

OBESITY IN MICE AND CHICKENS WITH AD-36 INFECTION

|  | Visceral Fat % increase | % fat INF vs CON |
|---|---|---|
| Chickens Exp 1 | 100% | 69% |
| Chickens Exp 2 | 129% | 64% |
| Chickens Exp 3 | 72% | 70% |
| Mice | 67% | 60% |
| Marmosets | 66% | 100% |

FIGURE 1

AD-36 IN MARMOSETS: Serum cholesterol

AD-36 ANTIBODY STATUS AND SERUM LIPIDS

|  | Cholesterol (mg/dl) | | Triglycerides (mg/dl) | |
| --- | --- | --- | --- | --- |
|  | AB- | AB+ | AB- | AB+ |
| Florida | 211 ± 5.8 | 175 + 9.8[a] | --- | --- |
| New York | 205 ± 7.2 | 171 ± 8.0[a] | --- | --- |
| Wisconsin | 216 ± 3.5 | 192 ± 4.6[a] | 151 ± 6.2 | 114 ± 6.5[b] |
| Combined sites | 213 ± 2.8 | 179 ± 4.4[b] | 151 ± 6.2 | 114 ± 6.5[b] |

Mean ± SEM; [a]$p<0.003$; [b]$p=0.0001$

FIGURE 8

VIRAL ANTIBODIES IN HUMANS IN OBESE VS NON-OBESE HUMANS

|  | OBESE AB+/AB- (%) | NON-OBESE AB+/AB- (%) |
|---|---|---|
| Florida | 28/75 (27%) | 5/30 (14%) |
| New York | 43/31 (57%) | 4/39 (9%) |
| Wisconsin | 37/146 (20%) | 7/57 (11%) |
| Totals | 108/254 (30%) | 16/126 (11%) |

FIGURE 7

CHARACTERISTICS OF 26 TWIN PAIRS DISCORDANT FOR AD-36

|  | Antibody + | Antibody − |
|---|---|---|
| Age (yr) | 33.0 ± 15.7 | 33.0 ± 15.7 |
| Sex (% F/M) | 77% / 23% | 77% / 23% |
| BMI: (kg/m$^2$) | 24.5 ± 5.2 | 23.1 ± 4.5* |
| Body fat (%) | 29.6 ± 9.5 | 27.5 ± 9.9* |

ADENOVIRUS - 5 INDUCES OBESITY IN MICE

Results at 27 wk after inoculation:

|  | Control | Ad - 5 infected |
|---|---|---|
| Body wt gain | 18.8 gm | 21.8 gm |
|  | (17.3 - 19.8) | (18.8 - 25.0) |
| % Body fat | 2.4% | 6.7% |
|  | (0.85 - 5.65%) | (3.10 - 11.20%) |

So, et al, Int J Obesity '05

FIGURE 12

BODIPY staining of 3T3-L1 cells 5-d post MDI treatment
A. Control, No Ad-36
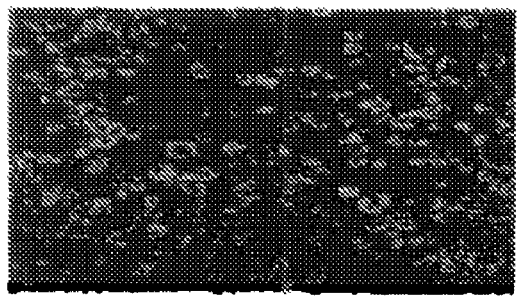
B. Ad-36 inoculated
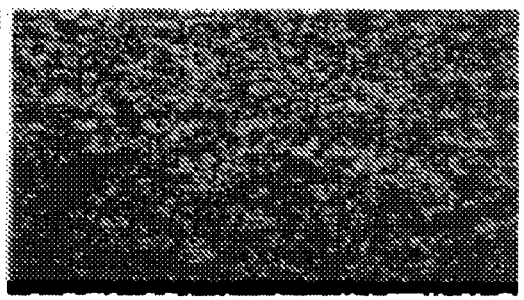
FIGURE 14

AD-36 STATUS IN RATS EXAGGERATES WEIGHT GAIN ON A HIGH FAT DIET

| % Fat in Diet: | Grams of weight gain | |
| --- | --- | --- |
| | Infected | Uninfected |
| 12% | -16 ± 5 | -11 ± 21 |
| 36% | 47 ±35 | 9 ± 22* |
| 48% | 22 ±45 | 10 ± 21 |
| 60% | 6 ± 45 | 9 ±18 |

AD-36 STATUS PREDICTS RESPONSE TO DRUG TREATMENT OF OBESITY

|  | Weight loss (lb) |
|---|---|
| Female: AB- | -33.9 + 18.8 |
| Female: AB+ | -35.8 + 21.8 (+6%) |
| Male: AB- | -31.1 + 19.2 |
| Male: AB+ | -58.7 + 26.4* (+89%) |

+ SD, *p<.02

Ad-36 infected males lost 89% more weight than uninfected

FIGURE 17

SEQUENCE LISTING

<160> NUMBER OF SEQ ID NOS: 4

<210> SEQ ID NO 1
<211> LENGTH: 1089
<212> TYPE: DNA
<213> ORGANISM: Adenovirus type 36

<400> SEQUENCE: 1

```
atgtcaaaga ggctccgggt ggaagatgac ttcaaccccg tctacccta tggctacgcg      60
cggaatcaga atatcccctt cctcactccc cccttttgtct cctccgatgg attccaaaac    120
ttccccctg gggtcctgtc actcaaactg gctgatccat gtctcactca aggtgggagg     180
gggactcact gtagaacaac agtctggaaa actgagtgtg atactaagg caccctttgca    240
agttgcaaat gacaacaaat tggagctatc ttatgatgat ccatttaagg tagagaataa    300
caaacttgga attaaagctg ccatggtttt agcagttgta actaaagaaa acacaagtct    360
tcctagtcta gttggaacac ttgtagtttt aactggaaaa ggaataggta ctggatcaag    420
tgcacatgga ggaactattg atgtaagact tggtgaagga ggtgggtatc atttgatgaa    480
aaaggagact tagtagcttg gacaaaaaaa atgatacac gcacccttg gacaacacct     540
gatccttctc caaattgcaa agttgaaaca gcaagagact caaagctaac cttagcactt    600
acaaaatgtg gtagtcaaat tttggccact gtatctttac ttgttgttac gggcaaatat    660
gctattataa gtgacacagt caacccaaag cagttctcta ttaagttact gtttaatgac    720
aagggtgttt tgttaagtga ctcaaatctt gatgggacat attggaacta tagaagcaac    780
aataacaaca taggcactcc ttataaagag gctgttggtt ttatgccaag cacaacagct    840
tatcctaagc caaccaacaa caccagcaca gatccggata aaaagagag tcaaggtaaa    900
aataaaattg taagcaatat atcttggagg agaggtatat caaccaggat ttattgttgt    960
taaatttaat caggaaactg atgccaattg tgcatactct attacatttg atttggatgg   1020
ggtaaggtgt ataaggatcc tataccatat gatacctctt ctactttctc atatatcgct   1080
caagaatga                                                            1089
```

<210> SEQ ID NO 2
<211> LENGTH: 25
<212> TYPE: DNA
<213> ORGANISM: Adenovirus type 36

<400> SEQUENCE: 2

```
agttgaaaca gcaagagact caaag                                            25
```

<210> SEQ ID NO 3
<211> LENGTH: 25
<212> TYPE: DNA
<213> ORGANISM: Adenovirus type 36

<400> SEQUENCE: 3

```
ggtactggat caagtgcaca tggag                                            25
```

<210> SEQ ID NO 4
<211> LENGTH: 28
<212> TYPE: DNA
<213> ORGANISM: Adenovirus type 36

<400> SEQUENCE: 4

```
ttgaaacagc aagagactca aagctaac                                         28
```

ADENOVIRUS STATUS AS A PREDICTOR OF BODY COMPOSITION CHANGE, DISEASE STATUS, AND TREATMENT OUTCOMES

CROSS-REFERENCE TO RELATED APPLICATIONS

This application claims priority to and the benefit of U.S. Provisional Application No. 60/715,182, filed Sep. 9, 2005, the disclosure of which is expressly incorporated herein by reference in its entirety.

BACKGROUND OF THE INVENTION

1. Field of the Invention

The invention relates generally to predictors of changes in body weight and disease status. Particularly, infection with obesifying adenoviruses in animals may be used to predict changes in body weight and disease status. More particularly, infection with certain adenoviruses, such as adenovirus type 36 (Ad-36) and adenovirus type 37 (Ad-37) may cause removal of the normal equilibrium factors that control fat cell metabolism and may make individuals more responsive than normal individuals to perturbations, which cause body composition change including weight gain or weight loss.

2. Related Art

Obesity is a serious disease of both humans and animals. A person is clinically obese if he or she has excess adipose tissue. Obesity has a number of known and suspected etiologies. There is a strong positive correlation of increased body weight with elevated serum levels of triglycerides (TG) and cholesterol (CHOL), including low-density-lipoprotein-associated cholesterol (LDL-CHOL). Thus, obesity, in its known forms, is often associated with elevated serum levels of these substances.

The prevalence of obesity is increasing worldwide. The prevalence in the US population during the 1960's was 13.5% rising to 15% in 1980. The prevalence in the US in 2000 was 21% and is still rising today. About 90 million people in the US are obese today. Similar statistics prevail in the rest of the world.

Obesity, in people who have the disease, is associated with physical, psychological, and social problems. Complications of obesity include, among others, diabetes mellitus, hypertension, hyperlipoproteinemia, cardiac diseases (atherosclerotic disease, congestive heart failure), pulmonary diseases (sleep apnea, restrictive lung disease), cerebrovascular accidents, cancers (breast, uterus, colon, prostate), gall bladder disease (stones, infection), toxemia during pregnancy, risks during surgery (pneumonia, wound infection, thrombo-phlebitis), gout, decreased fertility, degenerative arthritis, and early mortality.

Psychological complications of obesity include poor self-image and poor body-image. These complications are due in part to the fact that obesity is socially disfavored. The fact that obesity is socially disfavored also presents social problems for obese people. Among these is discrimination in jobs, education and marriage.

Clearly, there is a need for methods to treat or prevent obesity. Effective treatment or preventative methods likely vary among the obese depending on the etiology of the obesity which an individual has. Thus, there is a need to understand further the various etiologies of obesity. Such understanding will lead to methods and compositions to effectively treat or prevent the disease.

Further understanding of the etiologies of obesity also will lead to reduction in the prevalence of the social stigma associated with the disease, as it will allow the public at large to understand better that obesity is a disease which might afflict anyone and from which people do not choose to suffer. Such understanding also will allow obese persons to be convinced that they are unwilling victims of a disease, to understand through various diagnostic tests based on understanding of etiologies of the disease what the underlying cause of their obesity is, and in some cases to learn how to effectively treat the disease. Reduction in the prevalence of the social stigma associated with obesity and increased understanding among the obese concerning the disease will diminish the psychological complications and social problems which affect obese persons because of the disease.

Still further, understanding of the etiologies underlying obesity and the corresponding recognition that obesity is a disease eventually will lead medical insurance companies, which now at least in the United States typically do not recognize the condition as a disease, to recognize it as such and reimburse persons for diagnosis and treatment of it in the same way that the companies now do so for conditions that have long been recognized as diseases.

SUMMARY OF THE INVENTION

One aspect of the invention provides a method for predicting whether a subject on a regimen associated with weight loss and/or fat loss will have exaggerated weight loss and/or fat loss. The subject may be animal or human. The method may include obtaining a sample from the subject and determining whether the subject is infected with an obesifying virus. If the subject is infected with the obesifying virus, the subject will have an exaggerated weight loss and/or fat loss in comparison to the subject not infected with the obesifying virus. The sample may be a biological sample, body fluid, a tissue sample, an organ sample, feces, blood, salvia, and any combination thereof.

In a further aspect, the sample from the subject may be screened for the presence of antibodies specific to the obesifying adenovirus and then the analyzed for the presence of antibodies specific to the obesifying adenovirus in the sample. In particular, the antibodies may be specific to one or more peptides encoded by the nucleic acid sequences including SEQ ID NO.:1, SEQ ID NO.:2, SEQ ID NO.:3, and SEQ ID NO.:4. The screening step may be performed by using a method such as a serum neutralization assay or ELISA. In particular, the obesifying adenovirus may be adenovirus type 36 (Ad-36).

In a further aspect of the invention, the regimen associated with weight loss and/or fat loss may include administering the subject anti-obesity drugs. The anti-obesity drugs may include, for example, phentermine, fenfluramine, fluoxetine, sertraline, and phenylpropanolamine. In yet a further aspect of the invention, the regimen associated with weight loss and/or fat loss may include a calorie restricted diet. Additionally, the regimen associated with weight loss and/or fat loss may include a low fat diet.

Another aspect of the invention relates to predicting whether a subject on a regimen associated with weight gain and/or fat gain will have exaggerated weight gain and/or fat gain. The method may include obtaining a sample from the subject and determining whether the subject is infected with an obesifying virus. If the subject is infected with the obesifying virus, the subject may have exaggerated weight gain and/or fat gain in comparison to the subject not infected with the obesifying virus. The subject may be animal or human. The sample may be a biological sample, body fluid, a tissue sample, an organ sample, feces, blood, and salvia.

In a further aspect, the sample from the subject may be screened for the presence of antibodies specific to the obesifying adenovirus and then the analyzed for the presence of antibodies specific to the obesifying adenovirus in the sample. In particular, the antibodies may be specific to one or more peptides encoded by the nucleic acid sequences including SEQ ID NO.:1, SEQ ID NO.:2, SEQ ID NO.:3, and SEQ ID NO.:4. The screening step may be performed by using a method such as a serum neutralization assay or ELISA. In particular, the obesifying adenovirus may include adenovirus type 36 (Ad-36) or adenovirus type 37 (Ad-37).

The regimen associated with weight gain and/or fat gain may include a high fat diet. The high fat diet may include an eating regimen such that the daily fat intake is in the range of about 35% fat to about 48% fat.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced. In the drawings:

FIG. 1 is a table showing that Ad-36 infection in animals was a cause of obesity. This table demonstrates that in three chicken experiments, one mouse experiment, and one monkey experiment showed, that an infection with Ad-36 increased visceral fat by about 66% to about 129%. Of the animals infected, about 60% to about 100% became obese as compared to controls.

FIG. 6 is a table showing serum lipids in people infected with Ad-36 (AB+) versus people not infected with Ad-36 (AB−) in three US cities. Average cholesterol and triglycerides were lower in AB+ individuals than in uninfected individuals in all three cities.

FIG. 7 is a table showing the presence of serum antibodies to human Ad-36 in people from three US cities. An average of about 30% of obese people were infected with As-36 versus about 11% of non-obese who were not infected with Ad-36.

FIG. 8 is a table showing a comparison of twin pairs discordant for infection with Ad-36. Out of 89 twin pairs, 26 were discordant. The twins infected with Ad-36 were heavier and fatter than their uninfected co-twins.

FIG. 12 is a table showing human Ad-5 produced obesity in mice. Also, body fat increased by almost 3 fold.

FIG. 14 is a BODIPY staining of 3T3-L1 cells 5 days post MDI treatment. This figure shows triglycerides in 3T3-L1 cells infected with Ad-36 versus uninfected in vitro. Control cells show a moderate BODIPY fat stain whereas Ad-36 infected cells have about twice as much triglyceride, showing adipocyte biochemistry has changed.

FIG. 16 is a table showing the effects of Ad-36 status on rats differing levels of dietary fat. With low fat diet, infected rats lost slightly more weight, but with diets customarily considered high fat (about 36% to about 48% fat), infected rats had an exaggerated weight gain compared to controls. The about 60% fat diet is higher than usually eaten and both groups gained little weight.

FIG. 17 is a table showing Ad-36 status predicts response to treatment with obesity drugs. Ad-36 status was tested in 104 individuals treated with various obesity drugs for weight loss. Women infected with Ad-36 lost about 6% more weight than uninfected women. Infected men lost about 89% more weight, showing the exaggerated response to weight loss perturbations with infection.

DETAILED DESCRIPTION OF THE INVENTION

Figure 2:
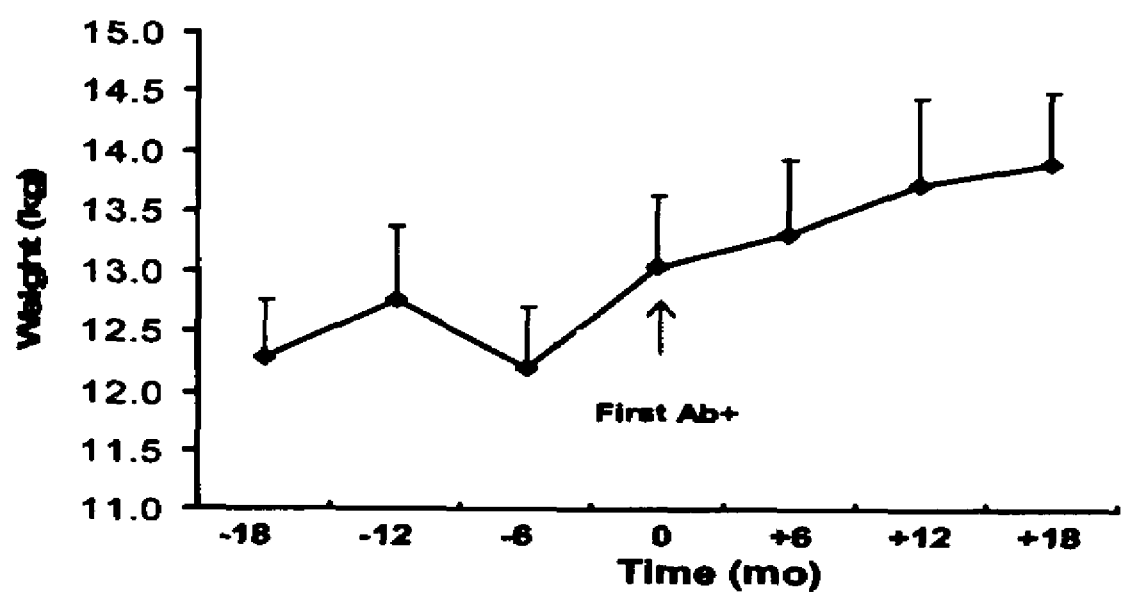
FIG. 2 is a graph showing the effects of spontaneous infection with Ad-36 in ad libitum fed rhesus monkeys. As compared to the period before a monkey became infected, once infection was noted (designated ↑) there was a steady rise in body weight that was still rising at about 18 months.
Figure 3:
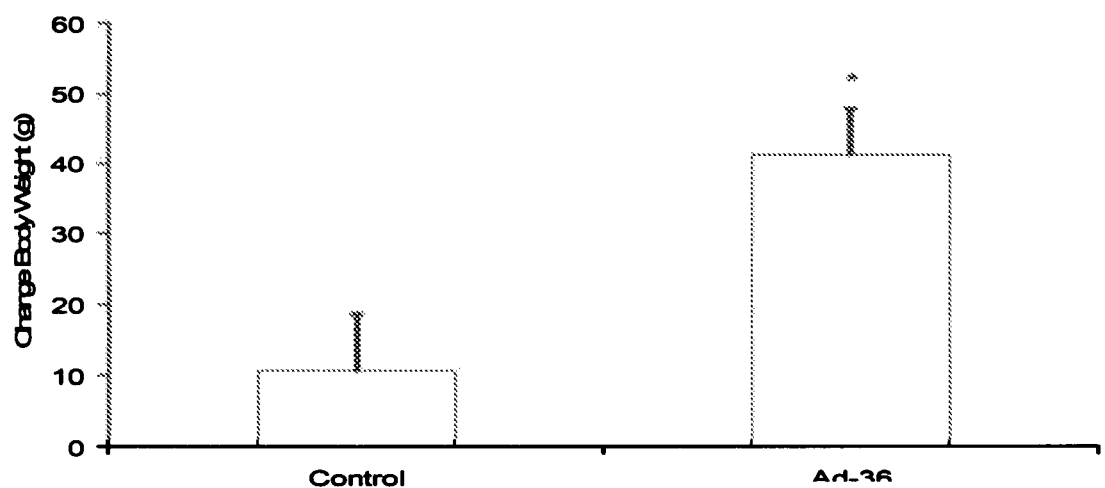
FIG. 3 is a graph showing an increase in body weight in monkeys infected with Ad-36. As compared to uninfected monkeys, infected monkeys gained about four times as much weight in about seven months.
Figure 4:
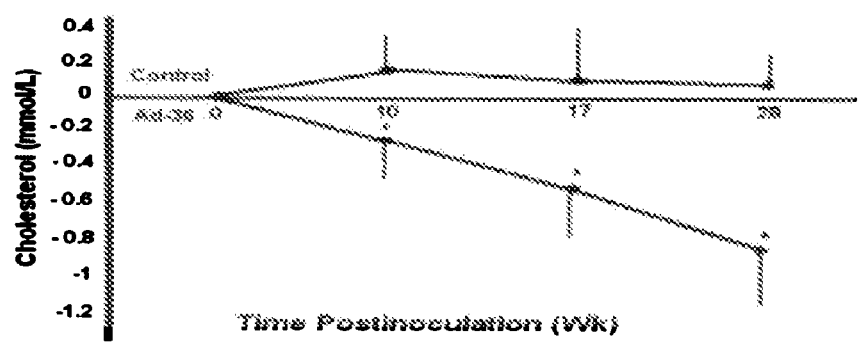
FIG. 4 is a graph showing a decrease in serum cholesterol in Ad-36 infected marmoset monkeys. Serum cholesterol began dropping immediately after infection and by about 10 weeks. This is significantly different than baseline in infected monkeys. There is no change in uninfected monkeys.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a virus" is a reference to one or more viruses and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and natures of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Moreover, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

Ad-5 is adenovirus type 5
Ad-21 is adenovirus type 21
Ad-36 is adenovirus type 36
Ad-37 is adenovirus type 37
TG is triglyceride
CHOL is cholesterol
LDL-CHOL is low density lipoprotein cholesterol
HDL-CHOL is high density lipoprotein cholesterol
SREBP is sterol regulatory element binding protein
PPAR-γ is peroxisome proliferation activated receptor-gamma
NASH is non-alcoholic steatohepatitis The term "body mass index (BMI)" refers to a statistical measure of the weight of a person scaled according to height. BMI may be defined as the individual's body weight divided by the square of the height and may be expressed in the unit $kg/m^2$. BMI may be used as a screening tool to identify possible weight problems for adults and children. However, in order to determine if excess weight is a health risk, a healthcare provider may need to perform further assessments, such as skinfold thickness measurements, evaluations of diet, physical activity, family history, hip to waist ratio, infection with an obesifying virus, and other appropriate health screenings. For adults about 20 years old and older, BMI may be interpreted using standard weight status categories that are the same for all ages and for both men and women. Alternatively, for children and teens, the interpretation of BMI is both age- and sex-specific. An adult having (i) a BMI in the less than about 18.5 may be considered underweight, (ii) a BMI in the range of about 18.5 to about 24.9 may be considered normal weight, (iii) a BMI in the range of about 25 to about 29.9 may be considered overweight, and (iv) a BMI greater than about 30.0 may be considered obese.

The term "hip to waist ratio" refers to a measurement that may be used to help determine obesity. The distribution of fat is evaluated by dividing the waist size by the hip size. For example, an individual with about a 30 inch waist and about a 40 inch hip size would have a ratio of about 0.75 and an individual with about a 41 inch waist size and about a 39 inch hip size would have a ratio of about 1.05. The higher the ratio, the higher the risk of heart disease and other obesity-related disorders.

A "biological sample" refers to a sample of tissue or fluid from a human or animal including, but not limited to plasma, serum, spinal fluid, lymph fluid, the external sections of the skin, respiratory, intestinal and genitourinary tracts, tears, saliva, blood cells, tumors, organs, tissue and sample of in vitro cell culture constituents.

An "isolated" or "substantially pure," nucleic acid (e.g., DNA, RNA, or a mixed polymer) for example, is one which is substantially separated from other cellular components which naturally accompany a native human or animal sequence or protein, e.g., ribosomes, polymerases, many other human or animal genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

The term "immunogenic," generally refers to an anti-obesity vaccine that has the capability to provoke in an immunized animal, an immune response that yields neutralizing antibodies against an obesity-causing, live virus that might infect the person after administration of the vaccine.

The term "antibody" refers to antibodies, digestion fragments, specified portions and variants thereof, including antibody mimetics or comprising portions of antibodies that mimic the structure and/or function of an antibody or specified fragment or portion thereof, including single chain antibodies and fragments thereof. The invention encompasses antibodies and antibody fragments capable of binding to a biological molecule (such as an antigen or receptor), such as the fiber coat protein of adenoviruses, and specifically, Ad-36, or portions thereof.

The invention relates generally to predictors of changes in body weight and disease status. Specifically, infection with specific adenoviruses in animals may be used to predict changes in body weight and disease status. Infection with certain obesifying adenoviruses, such as adenovirus type 36 (Ad-36) and adenovirus type 37 (Ad-37) may cause removal of the normal equilibrium factors that control fat cell metabolism and is known to make individuals more responsive than normal individuals to perturbations, which cause body composition change including weight gain or weight loss. Also, by testing individuals in various clinical settings for adenovirus status, the physician, for example, may predict the presence of disease, outcome of treatments, the occurrence of adverse outcomes, or the necessity for prevention measure to prevent adverse outcomes. The ability to predict changes in body composition and body weight, disease and progression of disease, outcome of treatment, and physical performance by testing viral status will be highly valuable to health professionals as well as to individuals.

In assignee's previous U.S. Pat. Nos. 6,664,050, and 6,127, 113, the disclosures of which are expressly incorporated herein by reference in their entirety, disclose methodologies to predict weight gain due to an infection with an obesifying virus, such as Ad-36. Moreover, it was disclosed that animals with adenovirus infection caused obesity in animals. Moreover, these obesity producing viruses may alter serum lipids including TG, HDL-CHOL, and LDL-CHOL levels in those who are infected. It was demonstrated that human Ad-36 increases body fat mass and paradoxically lowers lipids when inoculated into chickens, mice, rats, and monkeys (FIGS. 1-4).

Figure 5:
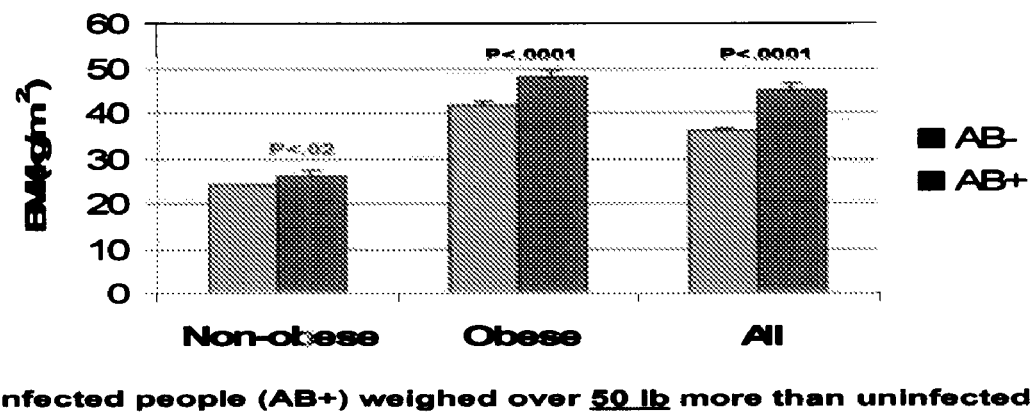
FIG. 5 is a chart showing body mass index in 502 individuals from three US cities according to status of infection with Ad-36. Overall, BMI was about 9 units higher in infected versus uninfected people (p<0.0001). Infected individuals of both obese and non-obese groups were significantly heavier than the uninfected in each group.
Figure 9:
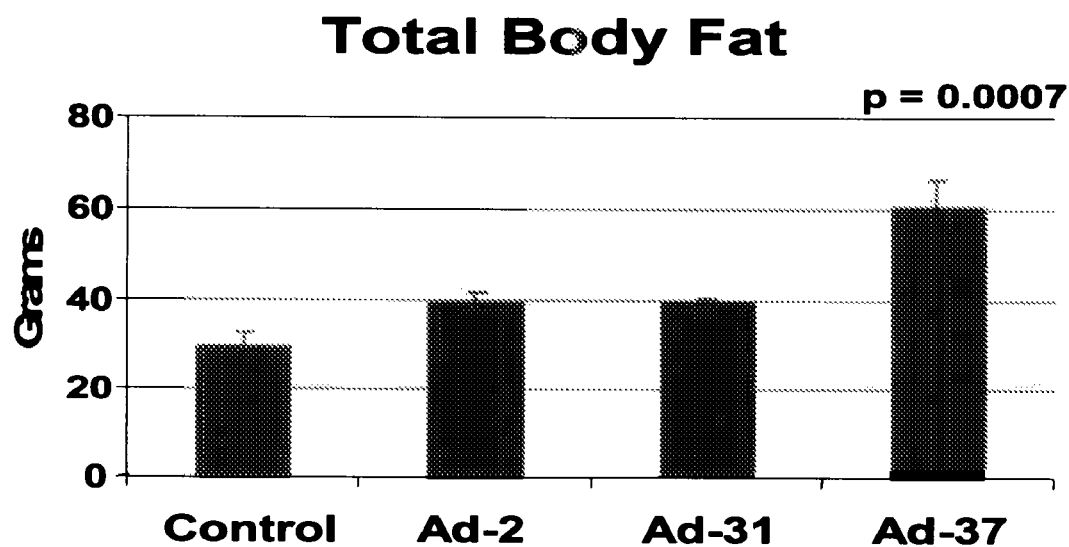
FIG. 9 is a chart showing the effects of multiple human adenoviruses on total body fat in chickens. Ad-2 and Ad-31 did not increase body fat, but Ad-37 had a marked effect.
Figure 10:
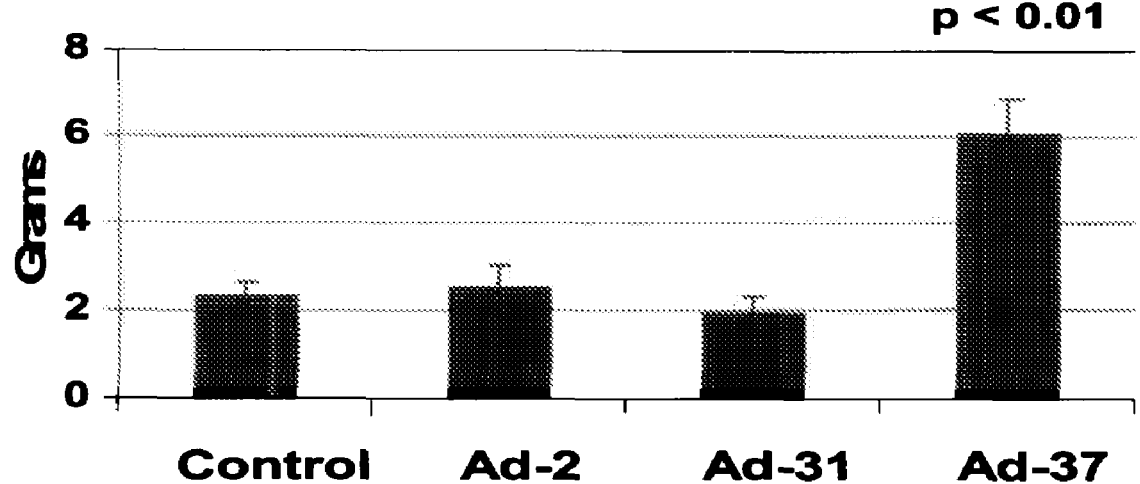
FIG. 10 is a chart showing the effects of multiple human adenoviruses on visceral fat in chickens. Ad-2 and Ad-31 did not increase visceral fat, but Ad-37 had a marked effect.

Human studies have also demonstrated that individuals infected with Ad-36 are heavier by about 9 BMI units (about 55 lb) and have significantly lower serum cholesterol and triglycerides (FIGS. 5-6). Moreover, it was demonstrated that about 30% of obese individuals and about 11% of non-obese individuals were infected with Ad-36 and that in twin pairs discordant for Ad-36, the infected twins were heavier and fatter than their co-twins (FIGS. 7-8).

Figure 11:
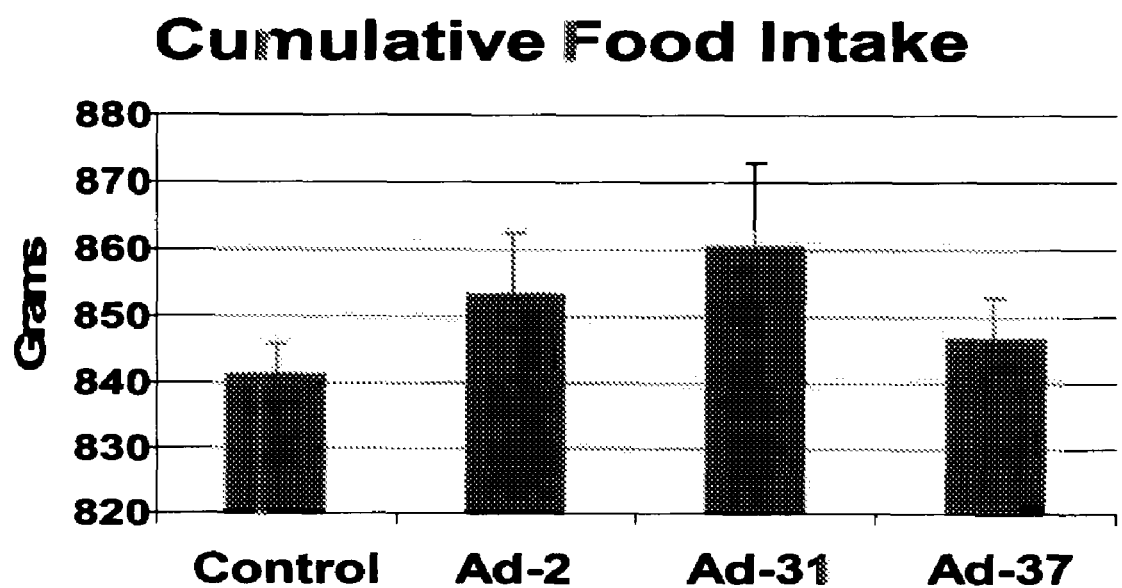
FIG. 11 is a chart showing food intake in animals exposed to multiple human adenoviruses. There were no differences in cumulative food intake among groups, yet individuals infected with Ad-37 became obese while individuals infected with Ad-2 or Ad-31 were not.

It has been demonstrated that infection with human adenoviruses Ad-36 and Ad-37 caused weight and/or fat gain in animals (FIGS. 1-8, FIGS. 9-11), and studies by So et al., 29(6) INT J OBES(LOND) 603-606 (2005), have shown that infection with Ad-5 caused weight gain in mice (FIG. 12). Other human adenoviruses may cause the same effects. The increase in body weight and fat with Ad-36 and Ad-37 occurred without an increase in food intake (FIG. 11). The mechanisms of the weight and fat gain are described below. Thus, one aspect of this invention is testing for status of human adenoviruses as a predictor of weight gain of individuals who have been infected therewith.

Figure 13:
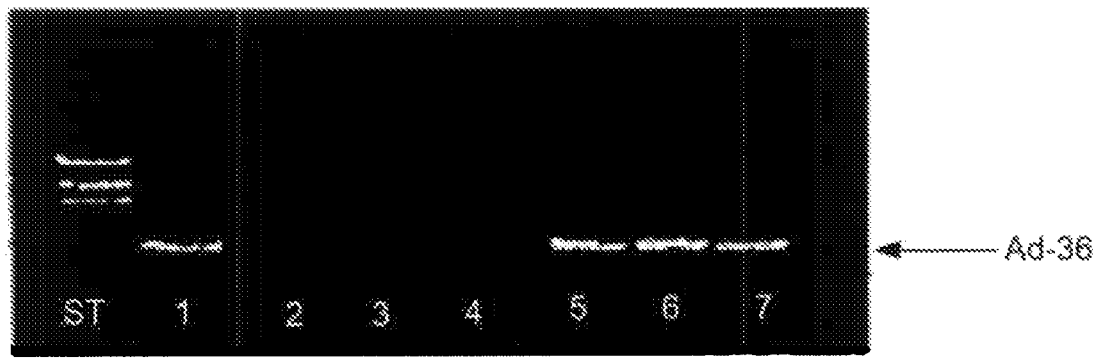
FIG. 13 shows the presence of Ad-36 DNA in adipose tissue of infected marmosets using a nested PCR assay. Lane 1 is Ad-36 DNA, lanes 2-4 show no Ad-36 DNA in fat of uninfected monkeys, and lanes 5-7 shows the presence of Ad-36 DNA in all infected monkeys.
Figure 15:
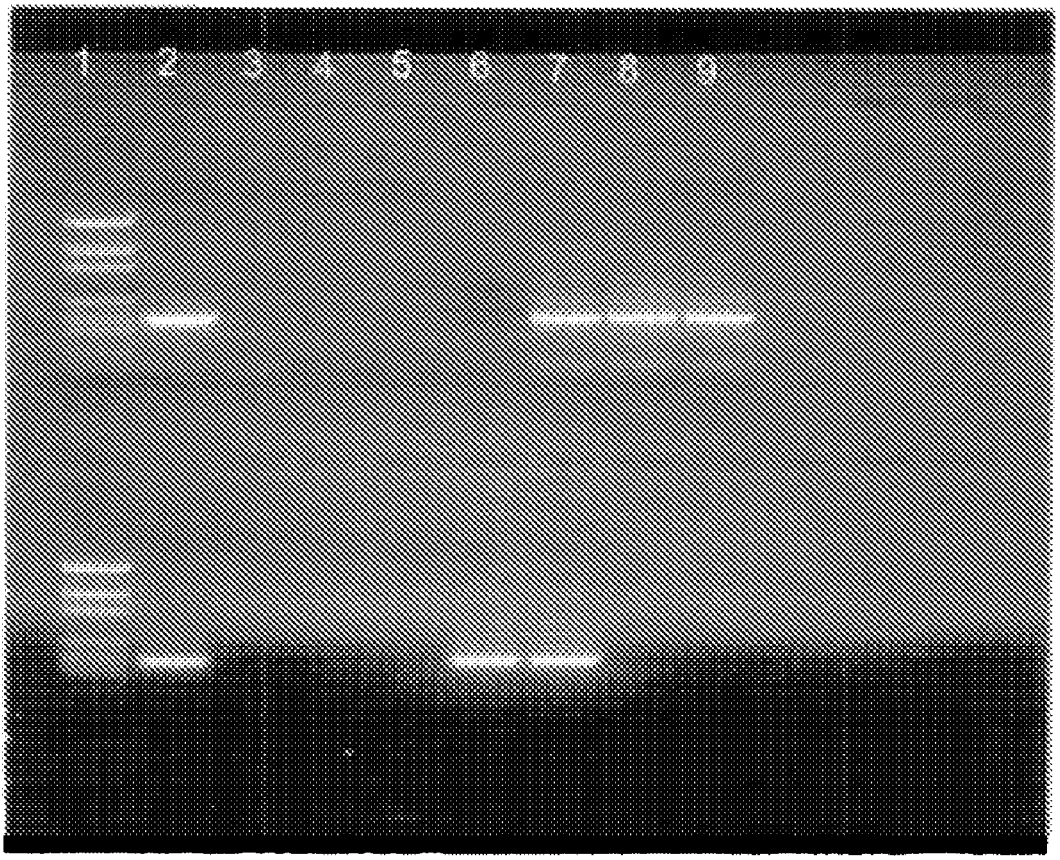
FIG. 15 is a gel showing Ad-36 DNA in adipose tissue of humans using nested PCR assay (bottom lanes). This gel shows Ad-36 DNA in adipose tissue of marmosets in the upper lanes (repeat of data in FIG. 13: lanes 4-6 negative from control marmosets, lanes 7-9 Ad-36 DNA from infected marmosets). In bottom lanes Ad-36 DNA is seen in 2 of 6 samples of human visceral adipose tissue obtained from cadavers at autopsy (lane 2 is positive control, lanes 6-7 are Ad-36 positive, lanes 4,5,8,9 are negative).

The mechanisms of weight and fat gain may be due to insertion of viral DNA into the cells of the body, which in turn, alter cellular biochemistry (See FIGS. 13-14). For example, it was demonstrated that Ad-36 DNA was present in fat cells of infected animals and humans and caused fat gain (See FIGS. 13-15). In fat cells, cellular biochemistry was altered in vitro and in vivo, resulting in accumulation of fat inside the cells (See FIG. 15). Additional studies have shown that enzymes responsible for fatty acid synthesis, including lipoprotein lipase, fatty acid synthase, SREBP, and PPAR-gamma were increased in cells infected with Ad-36 in vitro.

In one specific embodiment, the invention relates to predictors of weight gain and/or fat gain in animals. In particular, infection with adenovirus type 36 (Ad-36) may be associated with increase weight gain, fat gain and percent body fat as compared to uninfected animals when animals were fed a high fat diet (i.e., about 36% to about 48% fat) versus a low fat diet (i.e., about 12% fat). In situations that are obesifying, such as high fat diet, cessation of smoking, cessation of marked physical activity, the status of adenoviruses, such as Ad-36, may predict if individuals will gain excessive amounts of weight or fat thereby allowing preventive measures to be instituted.

An alternative embodiment of the invention relates to predictors of weight loss and/or fat loss. Specifically, infection status with adenoviruses, such as Ad-36 and/or Ad-37, has been shown to predict weight loss of individuals actively involved in an obesity drug regimen and with restricted calorie intake. Situations of weight loss treatment or perturbations by which weight loss may be expected will be exacerbated by the presence of adenovirus infection, such as Ad-36 and or Ad-37 infection. For example, viral infection status may be used to predict individuals who will have an exaggerated weight loss in response to drugs, dietary restrictions, or increased exercise. Also, individuals with infection, such as bacterial, viral, mycobacterium, retrovirus, and the like, or cancer may lose more fat and weight if they have been previously infected with certain adenoviruses, such as Ad-36 and/or Ad-37. In this case, these individuals may need preventive measures taken in advance to minimize the adverse outcome of weight loss and/or fat loss.

In yet a further embodiment, the invention relates to predictors of liver disease and response to treatment for liver disease. Individuals who gain fat have a higher prevalence of fatty liver disease, which may progress to liver cirrhosis. It has been demonstrated that infection with an avian adenovirus that causes obesity results in a fatty liver. Therefore, individuals who are infected with certain adenoviruses should be checked for liver disease more frequently and given more aggressive prevention measures for liver disease because they are at greater risk. For example, diabetics have a higher prevalence of fatty liver disease and should be checked more frequently and treated aggressively if adenovirus infection is present. A number of drugs, including alcohol, are associated with liver disease. Individuals taking drugs or alcohol who are infected are at higher risk for progression of liver disease and need close follow-up and preventive treatment if necessary, including stopping or changing or drugs.

Another embodiment of the invention relates to predictors of abnormal muscle function. Obese Individuals may experience pain while exercising and may need specialized prescriptions for regimens of physical activity. Infected individuals may have increased intracellular muscle fat and altered muscle function and may be more likely to have symptoms with exercise. Additionally, performance animals, such as race horses and greyhounds, which are infected with an obesity producing virus, may have increased intracellular muscle fat and compromised muscle function, thus decreasing their value for racing or other performance.

In another embodiment, the invention relates to an anti-obesity vaccine that may include as the active ingredient a composition (i) killed virus and inactivated live virus, where the corresponding live (non-inactivated) virus infects humans, and causes obesity and affects serum cholesterol and triglyceride levels in individuals infected with the virus; (ii) a coat protein of the coat of such a virus; (iii) an immunogenic peptide in the range of about 6 amino acids to about 30 amino acids in a sequence which includes the sequence of an epitope of such a coat protein; (iv) nucleic acid (DNA or RNA) with a sequence which encodes such a coat protein or such an immunogenic peptide; and (v) a non-pathogenic virus, such as a vaccinia virus or fowl-pox virus, which is genetically modified to have a modified coat protein which comprises in immunogenic position and orientation a segment with the sequence of a coat protein of a virus which infects humans and causes obesity and may affect serum cholesterol and triglyceride levels in infected individuals or a sequence of a peptide in the range of about 6 amino acids to about 30 amino acids in a sequence which includes the sequence of an epitope of a virus which infects humans and causes obesity and affects serum cholesterol and triglyceride levels in infected individuals.

The various active ingredients in the vaccines of the invention are either immunogenic or provide in vivo in a vaccinated person, a protein or peptide which is immunogenic. Peptides in the range of about 6 amino acids to about 30 amino acids, may be rendered acceptably immunogenic, might require modification by any of various techniques known in the art (e.g., conjugation with a large protein). A person of ordinary skill in the art would appreciate that the vaccines of the invention may be prepared by methods known in the art. The hexon or fiber proteins, specifically the fiber protein, or segments of the fiber protein, of Ad-36 may be used as the immunogen.

The anti-obesity vaccines of the invention, where the immunogenic component is live, inactivated virus, killed virus, coat protein, epitope-comprising coat protein segment, or coat protein (or epitope-comprising segment thereof) provided with use of a non-pathogenic, genetically modified carrier virus such as a vaccinia virus or a fowl pox virus, may be prepared using methods well known in the art.

The live viruses that may be employed in this method of the invention are obesity-causing, human adenoviruses, which may affect serum cholesterol and triglyceride levels, such as Ad-36, and their corresponding E1A fragments thereof. E1A fragments may be delivered intracellularly in a person being treated by methods known in the art using innocuous viruses, such as vaccinia viruses or retroviruses (modified so as to be non-infectious). The innocuous viruses used in accordance with the invention may have genomes that are modified to include DNA that encodes the E1A fragment in a position where the fragment will be expressed in cells of the individual that have been infected with the innocuous virus. The innocuous virus, so modified, may be administered to an individual being treated so as to infect the individual (and cells of the individual) with the virus. As described hereinabove, as known in the art, DNA itself (in an appropriate solution) which includes a segment that encodes the E1A fragment may be injected directly into an individual being treated to provide E1A intracellularly in the individual.

In an additional embodiment, the vaccines may include carriers, excipients, adjuvants, antimicrobials, preservatives and the like as well understood in the art. Thus, in addition to the active ingredient, the vaccines may have suitable compositions, usually aqueous buffers, such as phosphate-buffered saline or the like, in which the active ingredient may be suspended along with, optionally, any of various immune-system stimulating adjuvants used in human vaccine preparations, antimicrobial compositions, and other compositions to stabilize the preparations. All compositions included with the vaccine preparation may be suitable for administration to humans. The vaccine preparation may be stored in lyophilized form and then combined with solution soon before administration. For oral administration, the vaccine preparation may be in solution, tablet or pill form optionally with an enteric coating as understood in the art. The concentration of active (immunogenic or immunogen-providing) component in solution with which it is administered typically will be between about 1 ng and about 1 mg/ml.

The anti-obesity vaccines of the invention may be administered intranasally, orally, or by injection intravenously, intramuscularly, subcutaneously or peritoneally. Administration of the vaccines of the invention is to be under the guidance of a physician. Appropriate dosing of the anti-obesity vaccine is well within the skill of medical practitioners and will depend on a number of factors including the age of the person being treated, the urgency of the person's developing protective immunity, the status of the person's immune system, and other factors known to the skilled. The vaccine typically will be administered in several steps in order to cause and maintain protective immunity against obesity-causing virus in the person being vaccinated. Thus, after the primary vaccination, there typically will be between one and about ten booster vaccinations separated by periods between about 1 week and 10 years.

A single dose of an anti-obesity vaccine of the invention (in solution form) may have a volume in the range of about 0.1 ml to about 10 ml and, in any form, may have in the range of about 1 ng to about 10 mg of killed or inactivated obesity-causing virus, in the range of about 1 ng to about 10 mg of genetically modified, non-pathogenic virus, or in the range of about 1 ng to about 10 mg of coat protein (e.g., fiber protein) or in the range of about 6 amino acids to about 30 amino acid peptide (in its form as modified to be immunogenic).

An anti-obesity vaccine of the invention, where the active ingredient is nucleic acid, may also be a standard preparation for vaccines of that type. With vaccines of this type, the nucleic acid is not the immunogen but is expressed in vivo after administration of the vaccine as a peptide or protein which in turn is immunogenic. Vaccines of this type may be administered by techniques known in the art for such vaccines (e.g., intramuscular injection). Dosing will also be according to procedures known in the art to cause and maintain protective immunity against viral obesity in the vaccinated individual.

The anti-obesity vaccine according to the invention may include active ingredients based on more than one obesity-causing virus (or the coat protein (e.g. fiber protein) or epitopic segments of the coat protein thereof).

In yet another embodiment, the invention relates to a method of preventing obesity caused by a virus in a human or animal susceptible thereto which comprises administering to the human or animal an amount of an anti-obesity vaccine of the invention that is effective to raise and maintain a protective immune response against an obesity-causing adenovirus.

In still another aspect, the invention entails methods for screening body fluids or organs and tissues (especially donated blood or donated organs or tissues) for the presence of obesity-causing adenoviruses. These methods may include analyzing, by any conventional immunoanalytical or nucleic-acid probe hybridization based procedure, a sample of blood, other body fluid, feces, tissue or organ for the presence of antibody reflecting infection with the virus, the presence of a protein (e.g., a fiber protein) characteristic of the presence of the virus, or the presence of a nucleic acid fragment characteristic of the presence of the virus.

Exemplary screening immunoanalytical techniques include without limitation, standard virus neutralization assay techniques or enzyme immunoassay techniques well known in the art. Techniques for raising and purifying antibodies against these viruses or fragments thereof (e.g., fiber protein or fragments thereof), or proteins (or fragments thereof) from these viruses for use in these immunoassay techniques may be prepared by conventional techniques are well known in the art. In a specific embodiment of the invention, antibodies will immunoprecipitate adenovirus virus or adenovirus proteins from solution as well as react with these proteins on Western or immunoblots or polyacrylamide gels. In another specific embodiment, antibodies will detect the presence of adenovirus or adenovirus proteins in frozen tissue sections, using immunocytochemical techniques. Specific embodiments relating to methods for detecting adenovirus or adenovirus proteins include enzyme limed immunosorbent assays (ELISA), radioimmunoassay (RIA), immunoradiometric assays (IRMA) and immunoenzymatic assays (IEMA), including sandwich assays using monoclonal and/or polyclonal antibodies.

Similarly, the nucleic acid probe hybridization assay techniques used in these methods of the invention will be standard techniques (optionally after amplification of DNA or RNA extracted from a sample of blood, other body fluid, feces, tissue or organ) using nucleic acid probes (and primers if amplification is employed) made available by the obesity-causing viruses identified and made available by the present invention. The sequences of nucleic acids characteristic of these viruses can be determined by standard techniques once the viruses are conventionally isolated, and probes and primers that are specific for the viruses and that provide the basis for nucleic acid probes and primers that can be used in nucleic acid based assays for the viruses are prepared using conventional techniques on the basis of the sequences.

For example, in order to detect the presence of an adenovirus predisposing an individual to obesity, a biological sample such as blood is prepared and analyzed for the presence or absence of adenovirus proteins, such as the Ad-36 fiber coat protein sequences. Results of these tests and interpretive information are returned to the health care provider for communication to the tested individual. Such diagnoses may be performed by diagnostic laboratories, or alternatively, diagnostic kits are manufactured and sold to health care providers or to private individuals for self-diagnosis.

Initially, screening involves amplification of the relevant adenovirus sequences. In a specific embodiment of the invention, the screening method involves a non-PCR based strategy. Such screening methods include two-step label amplification methodologies that are well known in the art. Both PCR and non-PCR based screening strategies can detect target sequences with a high level of sensitivity.

One embodiment of the invention relates to target amplification. Here, the target nucleic acid sequence is amplified with polymerase. One specific method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, it desired to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the analyte. The region of the probes which is used to bind to the analyte can be made completely complementary to the targeted region of the adenovirus of interest, and in particular the fiber coat protein. Therefore, high stringency conditions are desirable in order to prevent false positives. However, conditions of hig stringency are used only if the probes are complementary to regions of the adenovirus. The stringency of hybridization is determined by a number of factors during hybridization and during the washing procedure, including temperature, ionic strength, base composition, probe length, and concentration of formamide.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and method for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes) enzymes, antibodies, gold nanoparticles and the like. Variations of this basic scheme are known in the art, and include those variations that facilitate separation of the hybrids to be detected from extraneous materials and/or that amplify the signal from the labeled moiety.

As noted above, non-PCR based screening assays are also contemplated by this invention. This procedure hybridizes a nucleic acid probe (or analog such as a methyl phosphonate backbone replacing the normal phosphodiester) to the low level DNA target. This probe may have an enzyme covalently linked to the probe, such that the covalent linkage does not interfere with the specificity of the hybridization. The enzyme-probe-conjugate-target nucleic acid complex can then be isolated away from the free probe conjugate and a substrate is added for enzyme detection. Enzymatic activity is observed as a change in color development or luminescent output resulting in about a $10^3$ to about a $10^6$ increase in sensitivity.

Two-step label amplification methodologies are known in the art. These assays work on the principle that a small ligand (such as digioxigenin, biotin, or the like) is attached to a nucleic acid probe capable of specific binding the adenovirus sequence region of interest. In one example, the small ligand attached to the nucleic acid probe is specifically recognized by an antibody-enzyme conjugate. In one embodiment of this example, digioexigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example i the biotin-avidin type interactions.

It is also contemplated within the scope of this invention that the nucleic acid probe assays of this invention will employ a cocktail of nucleic acid probes capable of detecting various species of adenoviruses. Thus, in one example to detect the presence of ad-36, ad-37 and/or ad-5, for example, in a biological sample, more than one probe complementary of the targeted regions of interest in the various types of adenovirus may be employed.

As the skilled will understand, more than one strain of obesity-causing virus may be tested for simultaneously in an immunological or nucleic acid-based assay method for testing for virus in accordance with the invention and kits may be assembled to facilitate carrying out the methods for a particular virus or a plurality of them.

Without further elaboration, it is believed that one skilled in the art, using the preceding description, can utilize the invention to the fullest extent. The following examples are illustrative only, and not limiting of the disclosure in any way whatsoever.

EXAMPLES

Example 1

Serum cholesterol (total)(TG) is determined using fasting serum, 10 µl samples, in a cholesterol-oxidase-peroxidase method employing a kit from Sigma Chemical Co., (St. Louis, Mo.). Serum TG is determined using fasting serum, 10 µl samples, in a glycerol-3-phosphate peroxidase method employing a kit from Sigma Chemical Co. Serum HDL-CHOL is determined using fasting serum with a kit from Sigma Chemical Co. LDL-CHOL is determined using the equation

LDL-CHOL=(CHOL)-(HDL-CHOL)-(TG/5)

Example 2

Ad-36 virus was obtained from the ATCC (American Type Culture Collection), Accession No. VR-913. The virus was grown in A549 bronchial human carcinoma cells (Wisconsin State Laboratory of Hygiene, University of Wisconsin, Madison, Wis.). Plaques were grown, and a single plaque was removed and used to reinfect a fresh batch of A549 cells. Plaques of this second passage were grown and again a single plaque was picked and used to reinfect another fresh batch of A549 cells. The resulting virus is a substantially purified form of Ad-36.

Example 3

Minimum Essential Media Eagle (MEM)(Sigma Chemical Co.) with non-essential amino acids, Earle's salts, 1-glutamine, 10% fetal bovine serum and 2.9% sodium bicarbonate (v/v), pH 7.4, was used for growing A549 cells. About 5 to about 10 µl of virus stock solution was mixed with 8 ml of the medium and the mixture was pipetted into flasks with growing cells. The flasks were incubated for about 1 h at about 37° C. while shaking gently about every 15 minutes. After about 1 hour, the medium was removed and replaced with fresh medium. The flasks were then incubated at about 37° C. The cells were grown over 7 to 8 days, until about 90% of the cells show CPE. The cell material and medium were then centrifuged at 1000 rpm for 15 min to eliminate cell debris. The supernatant containing the virus was centrifuged at 1000 rpm for 10 minutes and then aliquoted into 2 ml cryovials for storage at −70° C. until use.

Example 4

Fiber protein was isolated from virus in a two step procedure. First, virus was purified from supernatant (see Example 3) using CsCl gradient centrifugation as well known in the art. Then the fiber protein was isolated from the virus electrophoretically as well known in the art. The electrophoretic band of fiber protein (about 60,000 daltons) was cut from the gel and the fiber protein was isolated from the band by standard techniques.

Example 5

A virus neutralization assay (serum neutralization assay) was used to assay serum for antibody reactive with adenovirus in serum of test subjects. First, serum was thawed and heat-inactivated for about 30 minutes at 56° C. The assay was carried out in standard 96-well microtiter plates. Serial two fold dilutions (1:2 to 1:1024) were made with the medium that is the A549 growth medium described in Example 3 but lacks the fetal calf serum and sodium bicarbonate. 50 microliters of each dilution was added in duplicate to the wells of the plate. 50 microliters of virus suspension (100 $TCID_{50}$) was then added to each well. ($TCID_{50}$ was calculated by serially diluting viral stock solution and inoculating A549 cells with the dilutions to determine the reciprocal of the highest dilution of virus which causes CPE in 50% of the material inoculated.) The plates were then incubated at 37° C. for 1 hour. Then 100 microliters of A549 cell suspension, containing approximately 20,000 cells, was added to each well and the plate was further incubated at 37° C. for 12 days. Crystal violet-ethanol was then added to each of the wells to fix and stain the cells and the plates were examined macroscopically for CPE. The highest serum dilution with no CPE is the titer. Controls used in the procedure were wells with no virus and wells with virus but no serum. A back titration was carried out to confirm that appropriate virus dilutions were used. Positive control was antisera to chicken adenovirus and human adenovirus. Presence of CPE with the virus and no CPE in the presence of serum was considered an indication of effective neutralization of the virus with antibody in serum, such that the serum was considered to have antibody against the virus. A titer of 1:8 or greater was considered positive.

The foregoing assay was carried out on serum samples from 155 obese patients and 45 non-obese volunteers. 15-20% of the obese patients were positive for antibody. All of these had TG, CHOL, and LDL-CHOL within the normal ranges for non-obese people. The remaining obese people (antibody-negative) had, on the average, TG, CHOL and LDL-CHOL levels above the normal ranges for non-obese people. Approximately 11% of the non-obese volunteers were positive for antibody. The non-obese volunteers had, on the average, TG, CHOL and LDL-CHOL levels that were in the normal ranges for non-obese people.

Example 6

Ad-36 virus was killed by adding 42 µl of 37% formalin to 150 microliters of virus stock, then incubating the resulting composition at room temperature for 72 hours, and finally adding 15 microliters of 35% sodium bisulfite. Confirmation that the virus was killed is carried out by inoculating a culture of A549 cells with the final solution and determining that virus does not grow in the culture.

Example 7

Nucleic acid from adenovirus Ad-36 was isolated and sequenced by a standard sequencing method. The cDNA sequence encoding the fiber protein is as follows

SEQ ID NO: 1:
5'ATGTCAAAGAGGCTCCGGGTGGAAGATGACTTCAACCCCGTCTACCCC

TATGGCTACGCGCGGAATCAGAATATCCCCTTCCTCACTCCCCCCTTTGT

CTCCTCCGATGGATTCCAAAACTTCCCCCCTGGGGTCCTGTCACTCAAAC

TGGCTGATCCATGTCTCACTCAAGGTGGGAGGGGGACTCACTGTAGAACA

ACAGTCTGGAAAACTGAGTGTGGATACTAAGGCACCCTTGCAAGTTGCAA

ATGACAACAAATTGGAGCTATCTTATGATGATCCATTTAAGGTAGAGAAT

AACAAACTTGGAATTAAAGCTGGCCATGGTTTAGCAGTTGTAACTAAAGA

AAACACAAGTCTTCCTAGTCTAGTTGGAACACTTGTAGTTTTAACTGGAA

AAGGAATAGGTACTGGATCAAGTGCACATGGAGGAACTATTGATGTAAGA

CTTGGTGAAGGAGGTGGGTATCATTTGATGAAAAAGGAGACTTAGTAGCT

TGGGACAAAAAAATGATACACGCACCCTTTGGACAACACCTGATCCTTC

TCCAAATTGCAAGTTGAAACAGCAAGAGACTCAAAGCTAACCTTAGCAC

TTACAAAATGTGGTAGTCAAATTTTGGCCACTGTATCTTTACTTGTTGTT

ACGGGCAAATATGCTATTATAAGTGACACAGTCAACCCAAAGCAGTTCTC

TATTAAGTTACTGTTTAATGACAAGGGTGTTTTGTTAAGTGACTCAAATC

TTGATGGGACATATTGGAACTATAGAAGCAACAATAACAACATAGGCACT

CCTTATAAAGAGGCTGTTGGTTTTATGCCAAGCACAACAGCTTATCCTAA

GCCAACCAACAACACCAGCACAGATCCGGATAAAAAAGTGAGTCAAGGTA

AAAATAAAATTGTAAGCAATATATCTTGGAGGAGAGGTATATCAACCAGG

ATTTATTGTTGTTAAATTTAATCAGGAAACTGATGCCAATTGTGCATACT

CTATTACATTTGATTTGGATGGGGTAAGGTGTATAAGGATCCTATACCAT

ATGATACCTCTTCTACTTTCTCATATATCGCTCAAGAATGA-3'

Example 8

The cDNA sequence of the Ad-36p genome was screened against all known cDNA sequences and two 25-base sequences and one 28-base sequence were found, all lying in the fiber-encoding sequence provided above in Example 7, that were unique to Ad-36. These three sequences are as follows:

SEQ ID NO: 2:    5'-AGTTGAAACAGCAAGAGACTCAAAG

SEQ ID NO: 3:    5'-GGTACTGGATCAAGTGCACATGGAG

SEQ ID NO: 4:    5'-TTGAAACAGCAAGAGACTCAAAGCTAAC

Sequence 3 above was employed a probe for Ad-36 in a conventional nuclei acid probe hybridization assay of DNA isolated from four chickens, two of which had been infected with the virus and became obese and two of which had not been infected and were not obese. DNA hybridizing to the probe was observed with only the DNA from the two infected chickens. The assay involved direct detection and was by capillary electrophoresis using laser-induced fluorescence for detection. More particularly, a replaceable polyacrylamide matrix was employed in the electrophoretic separation and detection employed a dual system with 5'-labeling of the oligo and thiazole orange intercalator in the buffer system.

The skilled will understand that probes, and primers when amplification is also used, of between about 15 and 30 bases in length are advantageously employed to provide suitable specificity and sensitivity. Amplification methods using PCR and variations thereof maybe employed, as well known in the art.

Specific Example 9

Weight/fat Gain Exaggeration on Obesifying Regimens

In this example, the data show that obesity producing virus infections cause a higher amount of weight gain with regimens that are designed to cause obesity than occurs in uninfected controls. For example, rats were fed four levels of dietary fat: about 12%, about 36%, about 48%, and about 60%. It is well known that a high fat diet causes obesity compared to a low fat diet, and these data show that this effect can occur even without a change in energy intake. A very high fat diet, such as about 60% of calories as fat, is very unusual in people and is not usually preferred by most individuals. As seen in FIG. 16, the low fat diet caused a slightly greater weight loss in infected than in uninfected animals, but that the about 35% and about 48% fat diets caused a much higher weight gain in infected animals than in uninfected animals. A high fat diet is an example of an obesifying regimen and this phenomenon of exaggerated weight gain and/or fat gain in infected individuals may occur in any regimen or situation in which weight gain would be expected. Thus, testing for viral status as a predictor of exaggerated weight gain in humans and animal exposed to situations that would lead to weight gain may assist in minimizing adverse outcomes.

Specific Example 10

Weight/fat Loss Exaggeration on Regimens Associated with Weight/fat Loss

Figure 18:
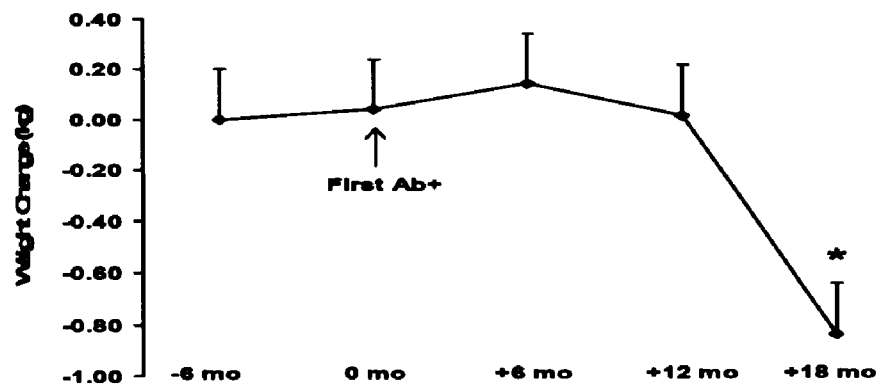
FIG. 18 is a graph showing the effects of spontaneous infection with Ad-36 in food restricted rhesus monkeys. The monkeys were restricted to about ⅓ less dietary intake than ad lib fed monkeys. As compared to the period before a monkey became infected, once infected was noted (designated ↑) there was a decrease in body weight that was not present in uninfected monkeys.

This example demonstrates that individuals infected with Ad-36 have exaggerated loss of weight as compared to uninfected individuals (See FIG. 18). 104 subjects treated with obesity drugs including phentermine, fenfluramine, fluoxetine, sertraline, and phenylpropanolamine were evaluated. The starting weights and maximum weight losses were calculated for individuals who were infected with Ad-36 versus individuals uninfected with Ad-36. There were 84 uninfected and 18 infected individuals. FIG. 17 shows that infected women lost about 6% more weight and infected men lost about 89% ($p<0.02$) more weight than did uninfected individuals. Another experiment was performed in monkeys who were calorie restricted and were infected with Ad-36. As noted above, ad libitum fed monkeys in this experiment gained weight with infection (See FIG. 2). In contrast, calorie restricted monkeys lost weight with infection (FIG. 18).

Finally, the experiment described above was also performed in rats. Here, rats were fed different amounts of dietary fat. The data demonstrated that infected rats that were fed the low fat diet (about 12% of kcal as fat) lost more weight than uninfected rats on the about 12% diet (See FIG. 16).

Thus, three experiments demonstrated that humans and animals that were infected with Ad-36 had an exaggerated response to perturbations that caused weight loss. Ad-36 DNA was demonstrated in the adipose tissue of animals and humans (See FIGS. 13 and 15). Alterations in the biochemistry of fat cells as described above were demonstrated. As noted above, changes in biochemistry of fat cells by viral DNA removes the normal equilibrium mechanisms from fat cells and allows exaggerated responses to both weight gain perturbations and weight loss perturbations.

In conclusion, the obesity producing adenovirus status of individuals, both animals and humans, can be used to identify those who will lose more weight in situations in which weight loss is expected. Thus, one aspect of the invention relates to testing for viral status as a predictor of exaggerated weight loss with perturbations that cause weight loss.

Specific Example 11

Liver Function

Figure 19:
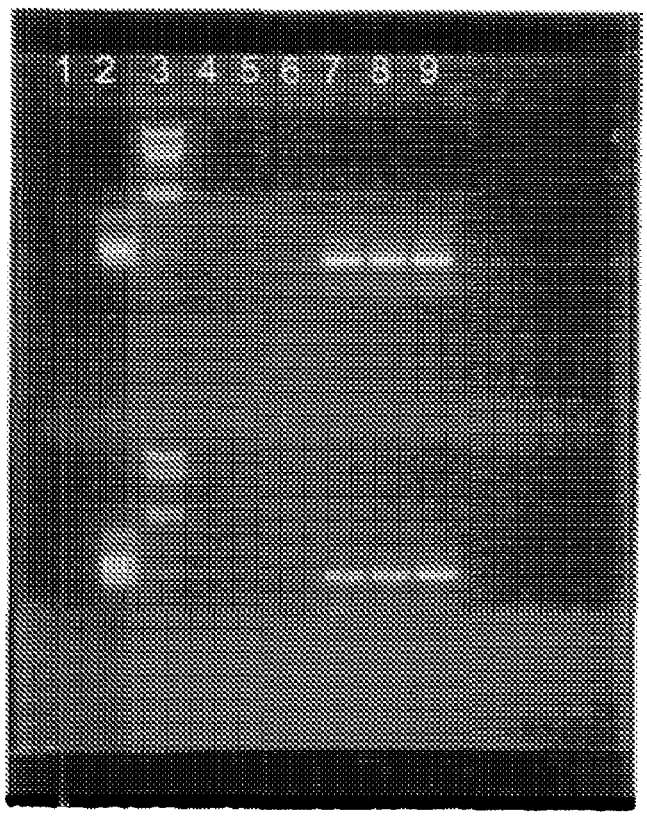
FIG. 19 is gel showing Ad-36 DNA in liver (upper lanes) and muscle tissue (lower lanes) of infected marmosets using nested PCR assay. Ad-36 DNA from infected monkeys is seen in lanes 7-9 of liver tissue and muscle tissue and is not present in lanes 4-6 from uninfected monkeys. Lane 2 is Ad-36 from culture, lane 3 is marker.

It has been demonstrated that chickens infected with an avian adenovirus had fatty livers. Ad-36 DNA was demonstrated in liver cells (See FIG. 19). The Ad-36 infection causes accumulation of fat in these cells; thus, altering the biochemistry of the cells, and results in a fatty liver, which may lead to a tendency for liver disease. Individuals with Ad-36 infection have a higher prevalence of fatty liver and a disease called non-alcoholic NASH. A high percentage of people with significant obesity have NASH. NASH is associated with a higher prevalence of cirrhosis and liver failure, and about one third of very obese individuals go on to cirrhosis. Since Ad-36 has been shown to cause obesity and obesity producing viruses cause fatty liver, it is possible to identify the presence of obesity producing viral infection to predict that fatty liver will progress to cirrhosis and liver failure is of immense importance to physicians and other health professionals. One aspect of this invention is testing for viral status as a predictor of both liver disease and outcome of liver disease.

There are many reasons for liver disease. If there is more than one reason for liver disease, outcomes are less favorable and progression to cirrhosis and liver failure is more likely. Since obesity induced viral infection causes underlying liver disease, it will be important for health professionals to know this if liver disease due to other factors is present. One aspect of this invention is testing for obesity producing viral status as a predictor for worse outcome in the presence of liver disease due to other factors.

Testing for obesity producing viruses may predict adverse events in response to drugs. Some drugs cause liver disease. The presence of underlying liver disease exacerbates the sensitivity of an individual to further liver disease when treated with drugs that can cause liver damage. By identifying underlying liver disease and predicting those individuals who will be more sensitive to adverse events with drugs, testing for viral status will greatly aid physicians and health professionals. One aspect of this invention is testing for obesity producing viral status as a predictor of adverse outcomes in response to drugs.

Specific Example 12

Muscle Function

Figure 20:
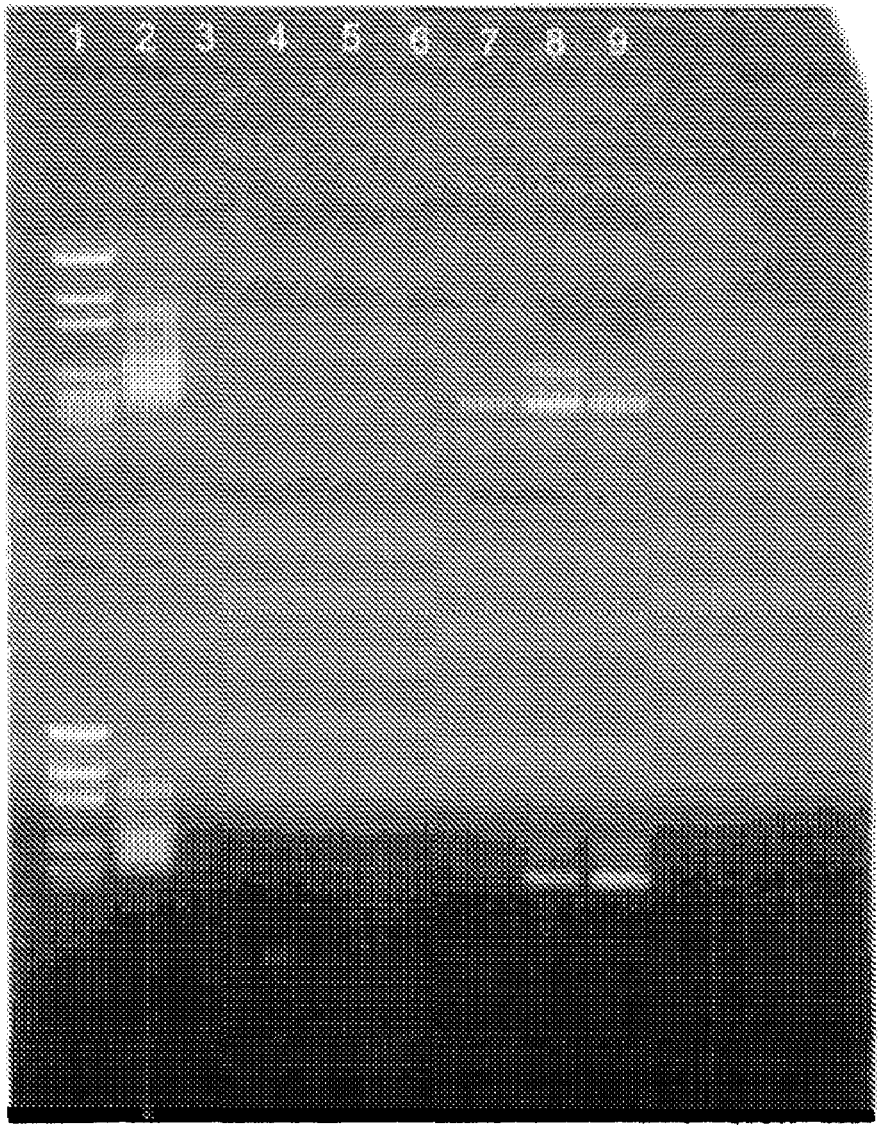
FIG. 20 is a gel showing Ad-36 DNA in muscle tissue of infected animals by nested PCR assay. Upper lanes are brain tissue from marmosets, lower lanes are muscle tissue. Ad-36 DNA from infected marmosets is seen clearly in lanes 8-9 and more faintly in lane 7. Ad-36 DNA is not present in lanes 4-6 from non-infected marmosets. Lane 2 is positive control from Ad-36 culture.

As obesity increases, the amount of fat inside the muscle increases. Infection with obesity producing adenoviruses results in viral DNA in muscle cells (See FIG. 20). This viral DNA alters the biochemistry of the muscle cell and produces increased fat inside the muscle and muscle cells. This increased fat and altered biochemistry produces decreased muscle performance in response to physical activity in infected individuals, both animal and human. A common complaint of obese people who try to exercise is that their muscles hurt. Individuals infected with obesity producing viruses will have a higher intramuscular fat and therefore are more likely than uninfected to have pain with muscle function and impairment of performance. Exercise regimens and physical activity prescriptions are adjusted for individuals who test positive for obesity viruses. One aspect of this invention is testing for obesity producing viral status as a predictor for individuals who need special attention in regard to physical activity regimens.

Also, it will be critical for buyers of performance animals to know viral status. For example, yearling race horses are not yet able to race, but buyers pay enormous sums of money for promising candidate champion horses with good bloodlines. If Ad-36 or other obesity producing adenovirus infection has altered muscle function even slightly by increasing intracellular fat, the horse may not be a champion. Similarly, racing dogs are quite expensive animals and should be tested for obesity virus infection. One aspect of this invention is testing for obesity producing viral status as a predictor of performance for racing and other performance animals.

Specific Example 13

Mechanisms of Effects of Obesity Producing Viruses on Liver and Muscle

Figure 21:
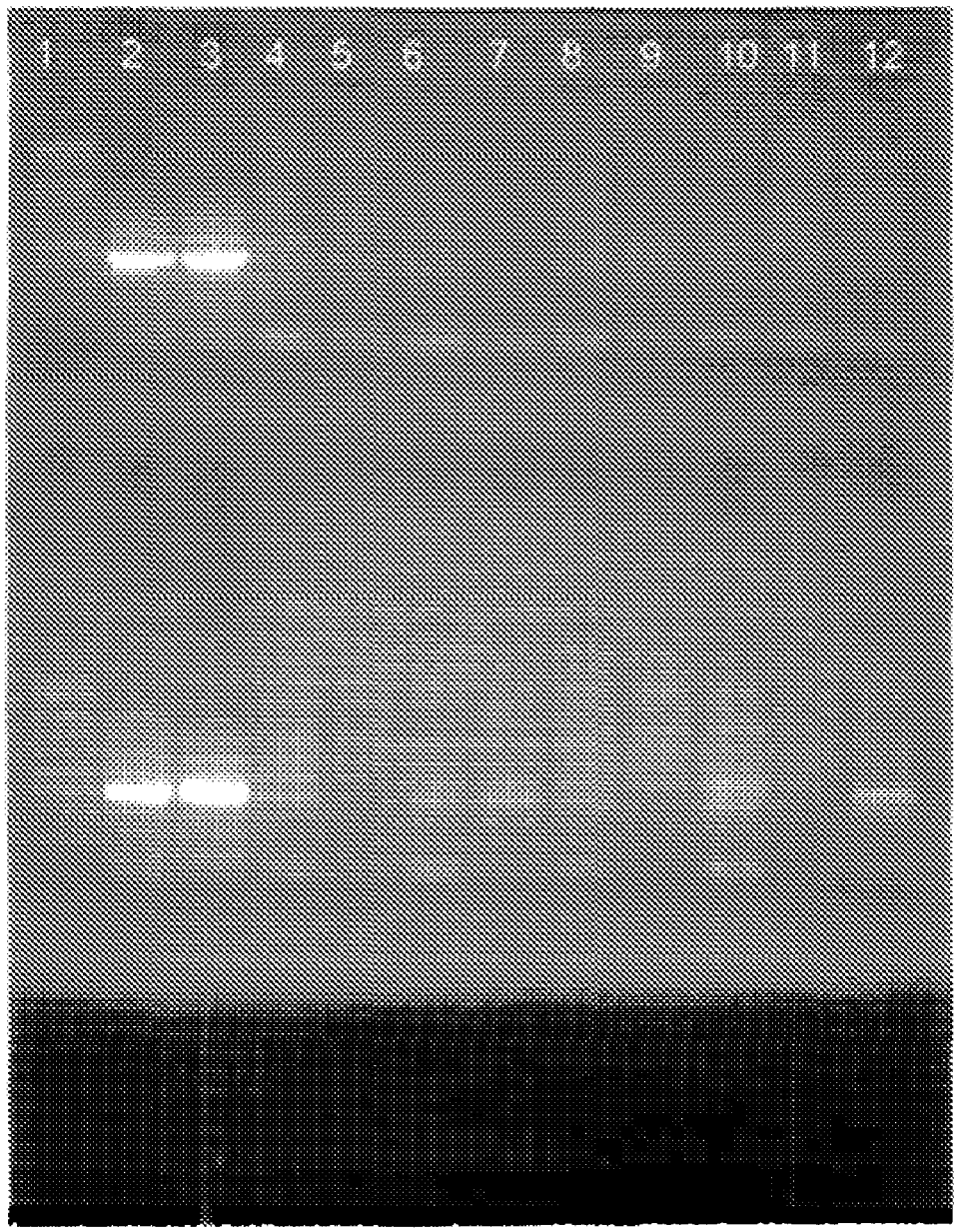
FIG. 21 demonstrates Ad-36 DNA in prostate tissue of humans by nested polymerase chain reaction assay of 18 samples of prostate tissue. 11 of the 18 samples show the presence of Ad-36 DNA. Lane 1: size marker, lanes 2-3: Ad-36 positive controls, and lanes 4-12: prostate tissue samples.

As described above, Ad-36 DNA was present in the fat cells of infected animals and altered the biochemistry of the fat cells. In addition to fat cells, it was demonstrated that Ad-36 DNA was recovered from cells of muscle, liver, brain, and lung of infected animals (See FIGS. 13, 19 and 20). It was also demonstrated that Ad-36 DNA was in fat cells and prostate tissue of humans (See FIGS. 15 and 21). Since it was demonstrated that Ad-36 DNA was present in many types of cells of the body, DNA of other human adenoviruses may be present as well. DNA of other adenoviruses will have the same effect on cellular biochemistry in fat, liver and muscle, because it has been shown that Ad-36, Ad-37 and Ad-5 changed fat cell biochemistry resulting in fat accumulation.

The examples given above are merely illustrative and are not meant to be an exhaustive list of all possible embodiments, applications or modifications of the invention. Thus, various modifications and variations of the described methods and systems of the invention will be apparent to those skilled in tie art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled molecular biology or in the relevant fields are intended to be within the scope of the appended claims.

The disclosures of all references and publications cited above are expressly incorporated by reference in their entireties to the same extent as if each were incorporated by reference individually.

What we claim is:

1. A method for predicting whether a subject infected with an obesifying adenovirus and on or about to start a regimen associated with a change in weight and/or body fat composition may have an increased likelihood of an increased change in weight and/or body fat composition in comparison to a subject not infected with the obesifying adenovirus, said method comprising the steps of:
   obtaining a sample from the subject on or about to start the regimen associated with a change in weight and/or body fat composition;
   assaying the sample to determine whether the subject has been infected with an obesifying adenovirus that indicates an increased likelihood of an increased change in weight and/or body fat composition; and
   modifying the regimen associated with the change in weight and/or body fat composition, as needed.

2. The method of claim 1, wherein said step of assaying the sample to determine whether the subject is infected with the obesifying adenovirus comprises the steps of:
   screening for the presence of antibodies specific to the obesifying adenovirus in the sample; and
   determining the presence of antibodies specific to the obesifying adenovirus in the sample.

3. The method of claim 1, wherein the obesifying adenovirus is adenovirus type 36 (Ad-36).

4. The method of claim 1, wherein the subject is afflicted with obesity.

5. The method of claim 1, wherein the increased change in weight and/or body fat composition is one of i) increased loss in weight and/or body fat composition; and ii) an increased gain in weight and/or body fat composition.

6. The method of claim 5, wherein the regimen is associated with weight loss and/or fat loss and comprises administering to the subject, anti-obesity drugs.

7. The method of claim 6, wherein the anti-obesity drugs is one or more drugs selected from the group consisting of phentermine, fenfluramine, fluoxetine, sertraline, and phenylpropanolamine.

8. The method of claim 5, wherein the regimen is associated with weight loss and/or fat loss and comprises a calorie restricted diet.

9. The method of claim 5, wherein the regimen is associated with weight loss and/or fat loss and comprises a low fat diet.

10. The method of claim 9, wherein the low fat diet includes an eating regimen such that about 12% kcal of the total daily caloric intake are fats.

11. The method of claim 1, wherein the subject is a human.

12. The method of claim 1, wherein the subject is an animal.

13. The method of claim 2, wherein the antibodies in said determining step are specific to one or more peptides encoded by the nucleic acid sequences selected from the group consisting of SEQ ID NO.:1, SEQ ID NO.:2, SEQ ID NO.:3, and SEQ ID NO.:4.

14. The method of claim 2, wherein said screening step is performed by using a method selected from the group consisting of serum neutralization assay and ELISA.

15. The method of claim 1, wherein the sample is selected from the group consisting of a biological sample, body fluid, a tissue sample, an organ sample, feces, blood, saliva, and any combination thereof.

16. The method of claim 5, wherein the regimen is associated with weight gain and/or fat gain and comprises a high fat diet.

17. The method of claim 16, wherein the high fat diet comprises an eating regimen such that the daily fat intake is in the range of about 35% fat to about 48% fat.

* * * * *